US009610254B2

(12) United States Patent
Csiszar et al.

(10) Patent No.: US 9,610,254 B2
(45) Date of Patent: Apr. 4, 2017

(54) MOLECULE MIXTURE COMPRISING AN AMPHIPATHIC MOLECULE TYPE A, WHICH HAS A POSITIVE TOTAL CHARGE IN THE HYDROPHILIC RANGE, AND AN AMPHIPATHIC MOLECULE TYPE B AND A POLYPHENOL C, METHOD FOR PRODUCING SAID MOLECULE MIXTURE AND USE THEREOF

(71) Applicant: FORSCHUNGSZENTRUM JUELICH GMBH, Juelich (DE)

(72) Inventors: Agnes Csiszar, Juelich (DE); Christian Kleusch, Bonn (DE); Bernd Hoffmann, Juelich (DE); Rudolf Merkel, Juelich (DE)

(73) Assignee: Forschungszentrum Juelich GmbH, Juelich (DE)

( * ) Notice: Subject to any disclaimer, the term of this patent is extended or adjusted under 35 U.S.C. 154(b) by 0 days.

(21) Appl. No.: 14/241,155

(22) PCT Filed: Oct. 1, 2012

(86) PCT No.: PCT/DE2012/000956
§ 371 (c)(1),
(2) Date: Feb. 26, 2014

(87) PCT Pub. No.: WO2013/050017
PCT Pub. Date: Apr. 11, 2013

(65) Prior Publication Data
US 2015/0037398 A1   Feb. 5, 2015

(51) Int. Cl.
| A61K 9/127 | (2006.01) |
| A61K 31/05 | (2006.01) |
| A61K 31/12 | (2006.01) |
| A61K 31/353 | (2006.01) |
| A61K 47/18 | (2017.01) |
| A61K 47/24 | (2006.01) |
| A61K 45/06 | (2006.01) |
| A61K 31/121 | (2006.01) |

(52) U.S. Cl.
CPC .............. *A61K 31/05* (2013.01); *A61K 9/127* (2013.01); *A61K 9/1272* (2013.01); *A61K 9/1277* (2013.01); *A61K 31/12* (2013.01); *A61K 31/121* (2013.01); *A61K 31/353* (2013.01); *A61K 45/06* (2013.01); *A61K 47/186* (2013.01); *A61K 47/24* (2013.01)

(58) Field of Classification Search
CPC ....................................................... A61K 9/127
USPC ........................................................ 424/450
See application file for complete search history.

(56) References Cited

U.S. PATENT DOCUMENTS

| 2005/0202076 A1* | 9/2005 | Mundus ............... A61K 9/1272 424/450 |
| 2008/0138400 A1* | 6/2008 | Kurzrock ............. A61K 9/1271 424/450 |
| 2008/0175895 A1* | 7/2008 | Kogure ..................... A61K 8/14 424/450 |
| 2009/0081282 A1 | 3/2009 | Oh et al. |
| 2010/0119593 A1 | 5/2010 | Liao et al. |

FOREIGN PATENT DOCUMENTS

| DE | 10 2010 002 969 | 11/2011 |
| EP | 1 932 517 | 6/2008 |
| EP | 2 123 259 | 11/2009 |
| EP | 2 451 441 | 5/2012 |
| JP | 2010-512384 | 4/2010 |
| WO | WO-2004/002468 | 1/2004 |
| WO | WO-2006/068759 | 6/2006 |
| WO | WO 2008/087803 | 7/2008 |
| WO | WO-2011/003406 | 1/2011 |

OTHER PUBLICATIONS

Date et al. (2011). "Lecithin-Based Novel Cationic Nanocarriers (Leciplex) II: Improving Therapeutic Efficacy of Quercetin on Oral Administration." Mol. Pharmaceutics, 8: 716-726.*
Movileanu et al. (2000). "Interaction of the antioxidant flavonoid quercetin with planar lipid bilayers." International Journal of Pharmaceutics, 205: 135-146.*
Sun et al. (2008). "The Bound States of Amphipathic Drugs in Lipid Bilayers: Study of Curcumin." Biophysical Journal, 95: 2318-2324.*
Ke et al. (2011). "Spectrometric Study on the Interaction of Dodecyltrimethylammonium Bromide with Curcumin." Langmuir, 27: 14112-14117.*
Kristl et al. (2009). "Improvements of cellular stress response in resveratrol in liposomes." European Journal of Pharmaceutics and Biopharmaceutics, 73: 253-259.*
Barry et al. (2009). "Determining the Effects of Lipophilic Drugs on Membrane Structure by Solid-State NMR Spectroscopy: The Case of the Antioxidant Curcumin." J. Am. Chem. Soc., 131: 4490-4498.*
Colin et al. (2011). "Endocytosis of Resveratrol via Lipid Rafts and Activation of Downstream Signaling Pathways in Cancer Cells." Cancer Prevention Research, 4(7): 1095-1106.*
Huh et al. (1996). "The Interaction of Polyphenols with Bilayers: Conditions for Increasing Bilayer Adhesion." Biophysical Journal, 71: 3261-3277.*
Phan et al. (2014). "Structure-dependent interactions of polyphenol with a biomimetic membrane system." Biochimica et Biophysica Acta, 1838: 2670-2677.*

(Continued)

*Primary Examiner* — Frederick Krass
*Assistant Examiner* — Amanda Heyes
(74) *Attorney, Agent, or Firm* — Jordan and Koda, PLLC (57) ABSTRACT

A molecule mixture comprising an amphipathic molecule of type A, which has an overall positive charge in the hydrophilic region, an amphipathic molecule of type B and a polyphenol C, the method for producing the molecule mixture, and the use thereof. The molecules of types A and B are present at a molecular ratio of A:B of 1(±0.2):1(±0.2) mol/mol. A method for producing the mixture and the use is also disclosed.

16 Claims, 3 Drawing Sheets

(56) References Cited

OTHER PUBLICATIONS

Date, A, A. [u.a.]: Lecithin-based novel cationic nanocarriers (Leciplex) II: Improving therapeutic efficacy of quercetin on oral administration. In: Mol. Pharm., 2011, vol. 8, S, 716-726.
Mehta, R.G., Murillo G., Naithani R. and Peng X., Pharm Res (2010) 24:950-961 Cancer Chemoprevention by Natural Products: How Far Have We Come?
Queen B.L., Tollefsbold T.O., Curr. Aging Sci. (2010). 3:34-42 Polyphenols and Aging.
Nair H.B. et al., Biochemical Pharmacology (2010), 80:1833-1843 Delivery of antiinflammatory nutraceuticals by nanoparticles for the prevention and treatment of cancer.
Kristl J. et al., European Journal of Pharmaceutics and Biopharmaceutics (2009), 73:253-259 Improvements of cellular stress response on resveratrol in liposomes.
Narayanan N.K., Nargi D., Randolph C., and Narayanan B.A., (2009), Int. J. Cancer. 125:1-8 Liposome encapsulation of curcumin and resveratrol in combination reduces prostate cancer incidence in PTEN knockout mice.
Chemistry and Physics of Lipids, 2010, vol. 163, p. 747-754.

\* cited by examiner

I.

II.

III.

MOLECULE MIXTURE COMPRISING AN AMPHIPATHIC MOLECULE TYPE A, WHICH HAS A POSITIVE TOTAL CHARGE IN THE HYDROPHILIC RANGE, AND AN AMPHIPATHIC MOLECULE TYPE B AND A POLYPHENOL C, METHOD FOR PRODUCING SAID MOLECULE MIXTURE AND USE THEREOF

BACKGROUND OF THE INVENTION

The invention relates to a molecule mixture comprising an amphipathic molecule of type A, which has an overall positive charge in the hydrophilic region, an amphipathic molecule of type B, and a polyphenol C, as well as to a method for producing the molecule mixture, and to the use thereof.

Polyphenols are secondary plant metabolites that occur in plant seeds, leaves and fruits. Some of these compounds have an inhibiting effect on cancer cells (Mentha, R. G., Murillo G., Naithani R. and Peng X., Pharm Res (2010) 24:950-961) or offer protection from undesirable oxidation processes (Queen B. L., Tollefsbold T. O., Curr. Aging Sci. (2010), 3:34-42). As a result, they are considered to be important constituents of human nutrition. Meanwhile, they are also important constituents in chemotherapy, since they have a toxic effect in extremely high concentrations. Given the high therapeutic relevance of polyphenols, the controlled and effective administration thereof to human beings is of great interest.

Administering such hydrophobic active ingredients in aqueous solutions has several drawbacks. First, a very high concentration is required to achieve a therapeutic effect. The majority of the active ingredient is present in a manner such that it is not accessible to the cells and, as a result, there is no cellular uptake of approximately 99% of polyphenols. Secondly, these ingredients lose their effect due to undesirable oxidation in aqueous environments.

Admittedly, liposomes and polymer capsules increase the bioavailability of polyphenols, given their more physico-chemical nature and hydrophilic properties, as compared to aqueous administration (Nair H. B. at al., Biochem. Pharmacology (2010). 80:1833-1843; Kristl J. at al., Eu. J. of Pharmaceutics and Biopharmaceutics (2009). 73:253-259; Narayanan N. K., Nargi D., Randolph C., and Narayanan B. A., (2009). Int. J. Cancer, 125:1-8), While these capsules offer advantages, the drawback is that controlled delivery and fast uptake of the polyphenol by the target cells are not ensured. In addition, these liposomes can protect the polyphenol only partially against undesirable oxidation processes.

SUMMARY OF THE INVENTION

Thus, it is the object of the invention to provide a molecule mixture in which the polyphenol is present in a stabilized manner and protected from oxidation processes. The polyphenol, or a mixture of polyphenols, is to be present in such a way that it can be introduced into living cells quickly and with high efficiency in a controlled manner, which is to say in the desired quantity, even in above-average quantities, and thereby achieve a targeted preventative, or a targeted toxic, effect on the cell. It is also an object of the invention to provide a method for producing the mixture and the use thereof.

The objects of the invention are achieved by the mixture according to the invention as described in the main claim, the method for producing the mixture, and the use of the mixture. Advantageous embodiments will be apparent from the respective claims referring to this claim, and in particular from claim 6, which claims the molecule mixture as a liposome.

The molecule mixture according to the invention comprises at least two types of molecules, A and B, and the polyphenol C.

The two types of molecules A and B are present at a molecular ratio of A:B of approximately 1:1. Minor deviations from the preferred ratio of 1:1 mol/mol are allowed, which is to say A:B of $1(\pm 0.2):1(\pm 0.2)$ mol/mol.

The molar ratio of the molecules of types A, B and of the polyphenol C should advantageously be approximately $1(\pm 0.2):1(\pm 0.2):0.1\text{-}25$ mol/mol, particularly advantageously $1(\pm 0.2):1(\pm 0.2):0.1\text{-}10$ mol/mol, and most advantageously $1(\pm 0.2):1(\pm 0.2):0.5\text{-}5$ mol/mol. In vitro proof of introduction of the polyphenol C into the target cell by way of a liposome has already been provided for the latter case.

Minor deviations from the ratio are allowed, as described above, provided that the repelling charges of molecule of type A are approximately compensated for by the neutral auxiliary molecules B. In vitro, the ratio of A:B:C starts to shift toward toxic concentrations at approximately 1:1:5 mol/mol for the polyphenol C.

It goes without saying that corresponding intermediate values must be allowed for the respective molecules of types A and B, which is to say, for example, 0.8, 0.9, 1.0, 1.1 and 1.1 in each case for the molecule of type A and the molecule of type B and, in turn, the intermediate values thereof. The same applies to the polyphenol C, which is to say all numerical values of 0.01, 0.02, 0.03, 0.04, . . . 24.98, 24.99 and 25.00 should be allowed in free combination with the described numerical values in the mixture with the molecules of types A and B, as long as rapid incorporation of the polyphenol C into the target cell from a mixture, and more particularly from the liposome into the cell, is ensured.

It was further recognized as part of the invention that polyphenols can be much better trapped and incorporated into target cells and the membranes thereof by way of positively charged liposomes that are produced from the mixtures according to the invention, than if one were to start with neutral liposomes, as was done in the cited prior art described in Kristl et al. With that production method, since the polyphenol was not added until after production of the liposome in an aqueous phase, only minor charging of the liposome with resveratrol occurred, substantially on the surface of the finished liposome. In contrast, according to the invention, the polyphenol is already added during production of the liposome from the dried mixture. The polyphenol thus represents an essential constituent in the liposome membrane and is introduced therein to a high degree. This advantageously results in controlled, targeted, and complete charging of the liposome with the polyphenol C. It was also recognized as part of the invention that the polyphenol in the liposome membrane then itself triggers fusion with the membrane of the cell. This advantageously causes the polyphenol to be transferred quickly into the target cells with high efficiency.

Moreover, it was found that the polyphenol that is present in the membrane of the developing liposome is well-protected from preliminary oxidation processes.

It was found that, with the method of producing the mixture, polyphenols generally dissolve easily in organic solvents such as ethanol or chloroform, and that these can therefore suppress preliminary oxidation of the polyphenol.

The dissolved polyphenol is thus mixed with the neutral and positively charged lipids of the molecules of types A and B in at least one organic solvent, so as to provide the mixture according to the invention. This is done so as to homogenize the molecule mixture.

It goes without saying that the mixture is advantageously present in powdered, homogenized form after the organic solvent has been removed. This in itself already achieves the object of the invention.

As with the mixture, the molecular ratio A:B to be selected for the production method should correspondingly be $1(\pm0.2):1(\pm0.2)$ mol/mol. The molar ratio of the positive and neutral lipids of the molecules of types A, B and of the polyphenol C should advantageously be, or be adjusted to, approximately $1(0.2):1(\pm0.2):0.1-25$ mol/mol, particularly advantageously $1(\pm0.2):1(\pm0.2):0.1-10$ mol/mol, and most advantageously $1(\pm0.2):1(\pm0.2):0.5-5$ mol/mol. Minor deviations are therefore allowed, as mentioned above.

The mixture according to the invention, which is preferably defined as a liposome, and the drug based on the mixture according to the invention, in particular the liposome-based drug, to be used thus comprise the molecule of type A, a molecule of type B and a polyphenol C in the indicated ratio.

In a further particularly advantageous embodiment of the invention, the bioavailability of the polyphenols is particularly advantageously increased for therapeutic purposes, while offering protection against oxidation, by way of the transfer from the organic phase via the powdered phase into the aqueous, liposomal environment.

The molecule mixture according to the invention comprising the molecules of types A and B together with the polyphenol C is thus separated from the organic solvent, or the organic solvents, and gently transferred into an aqueous buffer having a pH of approximately 7. This means that, for the production of the liposome, the organic component is essentially replaced with an aqueous system that is based on a physiological buffer.

It is not until the aqueous environment that the particularly preferred multilamellar, self-closed spherical structures form, which are referred to as liposomes. The liposomes can be homogenized further by additional steps such as ultrasonic treatment, extrusion or multiple cooling and heating of the solutions down to 4° C. and up to 70° C. These structures have a positive charge (zeta potential Uz=30 to 100 mV) due to the molecule of type A. The majority of non-polar polyphenols are located in the interior of the lipid bilayers, or of the liposome membrane, and are thus advantageously shielded and protected from reactive oxygen radicals. Such liposomes are to be formed from all mixtures according to the invention.

These liposomes according to the invention, which are charged with polyphenol, fuse very efficiently with the plasma membrane of animal cells, as a result of the interaction between the positively charged lipids and the delocalized electrons of the plant polyphenols, by way of simple surface contact, over just a few minutes (5 to 20 minutes).

If the mixture is present as a liposome, the majority of the polyphenol C will be present introduced into the liposome membrane. Only a smaller portion of it will be dissolved in the interior of the liposome itself in an aqueous buffer. As a result, the polyphenol itself triggers fusion with the target cell membrane.

The phenols themselves are oxidized during the therapeutic use, rather than the cellular molecules. The presence of the polyphenols thus advantageously prevents overoxidation of the cell. The mixture according to the invention and the drug made therefrom are thus effective therapeutic agents for treating all oxidative disease processes or certain cancer diseases.

If large quantities of these radical scavengers are to be present in vitro in the mixture, or in the liposome, values having a molar ratio of approximately 1:1:5 mol/mol of the molecules of types A and B and of the polyphenol C may be used or administered. This mixture then has a rather toxic effect. Such a high, or an even higher, quantity is thus proposed for cancer therapies so as to overoxidize cancer cells to a high degree and thereby kill them. In vivo, other concentrations are possible and must be considered.

The mixtures and positively charged liposomes must thus comprise a molecule of type A and a molecule of type B. The criteria for the molecule of type A are that (a) the molecule includes a hydrophilic region having at least one or more positive charges, so that the overall charge of the hydrophilic part of the molecule is positive. The role of this molecule is to bring the fusion mixture into the vicinity of the negatively charged cell membrane by way of electrostatic forces. (b) The molecule of type A further includes a hydrophobic region, preferably a C10-C30 component with or without double bonds. Double bonds have the advantageous effect that the membrane of the resulting liposome becomes elastic, whereby the fusion of the liposome with the cell membrane is facilitated. Suitable molecules are, for example, 1,2-dioleoyl-3-trimethylammonium propane (DOTAP), N-(2,3-dioleyloxypropyl)-N, N, N-trimethylammonium chloride (DOTMA), dimethyl dioctadecyl ammonium bromide (DDRB) or (1-[2-(oleoyloxy)ethyl]-2-oleyl-3-(2-hydroxyethyl)imidazolinium chloride (DOTIM). DOTAP (1,2-dioleoyl-3-trimethylammonium propane (chloride salt)) is mentioned as a first example.

The criteria for molecules of type B are that (a) the molecule must include a hydrophilic region and (b) a hydrophobic region (in particular C10-C30) with or without double bonds. For the function of the double bonds see type A. (c) The two regions should be neutral so as to neutralize the high charge density and the repelling forces between positively charged molecules of type A. This effect stabilizes the system. Molecules of type B are thus auxiliary molecules. Suitable molecules are, for example, phosphatidylethanolamines and phosphatidylcholines, such as 1,2-dioleoyl-sn-glycero-3-phosphoethanolamine (DOPE), 1,2-dipalmitoyl-sn-glycero-3-phosphoethanolamine (DPPE), 1,2-dimiristoyl-sn-glycero-3-phosphoethanolamine (DMPE), 1,2-dielaidoyl-sn-glycero-3-phosphoethanolamine (DEPS), 1,2-diphytanol-sn-glycero-3-phosphoethanolamine, 1,2-dilinoleoyl-sn-glycero-3-phosphoethanolamine or 1,2-dioleoyl-sn-glycero-3-phosphatidylcholine (DOPC).

The polyphenols used are molecules that comprise at least two hydroxyl groups bound directly to an aromatic ring, and are secondary plant metabolites. Polyphenols, such as resveratrol, curcumin, hydroxyflavone and genistein, are preferably selected in the indicated ratio for the mixture according to the invention and liposomes.

The invention will be described in more detail hereafter based on exemplary embodiments and the accompanying two figures, without thereby limiting the invention.

BRIEF DESCRIPTION OF THE DRAWINGS

FIG. 3 A shows that the positively charged liposomes without polyphenol.

FIG. 3 B shows that an increase in the polyphenol concentration which here is curcumin.

FIG. 3 C shows that the fusion rate after use of 5-hydroxyflavone-containing lliposomes.

DESCRIPTION OF THE PREFERRED EMBODIMENTS

Figure 1:
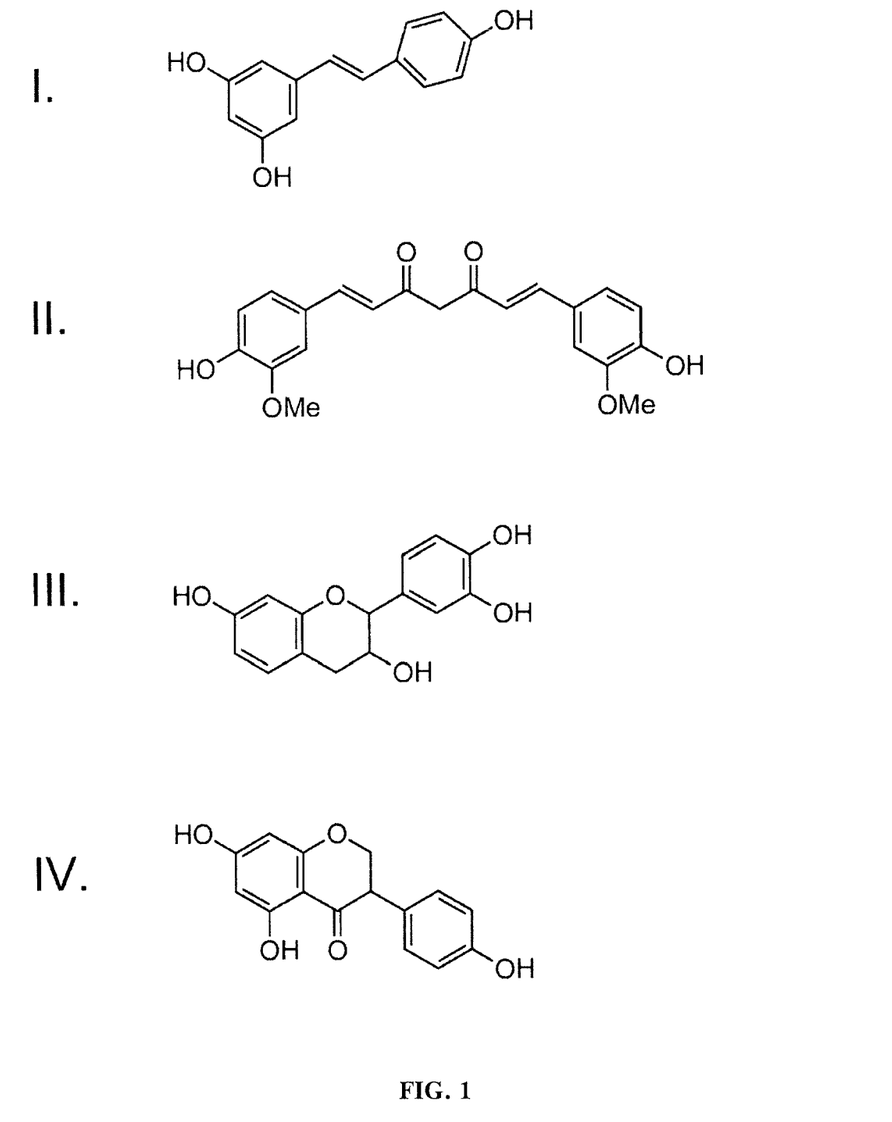
FIG. 1: shows structures of the preferred polyphenols: I. resveratrol. II. curcumin. III. hydroxyflavone. IV. genistein.

The chemical formulas illustrated in FIG. 1 are shown only by way of example of some particularly relevant and readily available polyphenols. However, other polyphenols not illustrated here shall be explicitly covered by the current claims. It therefore goes without saying that other polyphenols than those shown are also conceivable for the production and use of the mixtures and liposomes according to the invention.

1. Exemplary Embodiment

In Vitro Analyses with Cells 1,2-dioleoyl-3-trimethylammonium propane, chloride salt (DOTAP) as a positively charged lipid of molecules of type A, and 1,2-dioleoyl-sn-glycero-3-phosphoethanolamine (DOPE) as a neutral lipid of molecules of type B (Avanti Polar Lipids Inc., Alabaster, Ala., USA) and N-(4,4-difluoro-5,7-dimethyl-4-bora-3a,4a-diaza-s-indacene-3-propionyl)-1,2-dihexadecanoyl-sn-glycero-3-phosphoethanolamine (triethylammonium salt) (corresponds to BODIPY® FL-DHPE) (Invitrogen, Eugene, Oreg., USA) as a fluorescent marker lipid were placed in a chloroform/ethanol (10/1 vol/vol) solvent mixture at a molar ratio of DOTAP/DOPE/BODIPY FL-DHPE=1/1/0.005 mol/mol at a total lipid concentration of approximately 1 mg/ml, and mixed.

BODIPY® FL-DHPE is used here only for the purpose of detecting successful membrane fusion between the liposome and plasma membrane. Such dyes are explicitly not the subject matter of the mixture according to the invention or of the liposome according to the invention.

Resveratrol (Sigma-Aldrich, St. Louis, Mo., USA) was first dissolved in ethanol as the organic solvent at a concentration of 1 mg/ml and homogenized.

The lipid component made of molecules of types A and B and BODIPY® FL-DHPE was then mixed with resveratrol in the following molar ratio from the organic solvent mixture (Table 1).

The components were first homogeneously mixed in chloroform/ethanol. After the lipids had been mixed with the resveratrol, the organic solvents were dried under vacuum for 30 to 60 minutes and then once again placed in a buffer solution of 20 mM HEPES (pH 14) at a final concentration of approximately 2 mg lipid/ml buffer, and homogenized in an ultrasonic bath for 20 minutes. The emulsion is then present as a liposome, which holds for at least 4 weeks.

Figure 2:
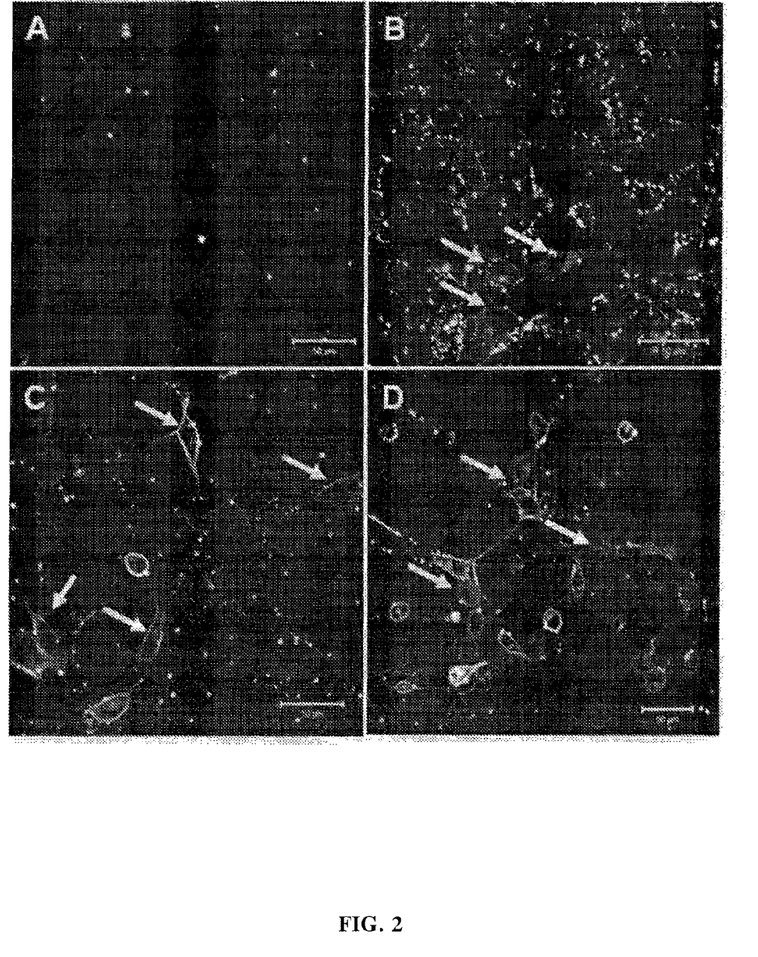
FIG. 2: shows the introduction of resveratrol into positively charged liposomes and the in vitro detection thereof in cells.

Treatment of 3T3 Cells with Resveratrol-Containing Liposomes:

10 µl of the resveratrol-containing liposomes was diluted 100-fold with RPMI medium (Sigma-Aldrich, St. Louis, Mo., USA) and treated again for 5 to 10 minutes with ultrasound (80 to 100 W) before being added to a cell culture dish containing 3T3 cells (20,000 to 30,000 per dish, (diameter=3.5 cm)). Afterwards the cells were washed with HEPES medium, and the fusion efficiency of the reagent with the cell membrane was examined under a fluorescence microscope. FIGS. 2 A to D show the corresponding results for experiments a) to d). The bar indicates 50 µm in each case.

The experiments and the associated illustrations show that very effective and homogeneous membrane fusion is induced starting at a molar ratio of total lipid/resveratrol of 2.005/1.25 (FIG. 2 C), which is indicated by the fluorescent green membrane marker BODIPY® FL-DHPE. In the black and white FIGS. 2 A to 2 D, this marker indicates the contours of the cells by dying of the membrane, some of them marked by the white arrows. With double the resveratrol concentration (FIG. 2 D), the cell morphology and number of marked cells are unchanged.

FIG. 2 A shows that the positively charged liposomes without resveratrol or a polyphenol (DOPE/DOTAP/BODIPY FL-DHPE 1/1/0.005 mol/mol) do not trigger any membrane fusion with 3T3 cells.

FIG. 2 B shows that the first inhomogeneous fusion can be observed starting at a resveratrol concentration of total lipid/resveratrol=2.005/0.62. Starting at this concentration, an effect of the polyphenol C as a therapeutic agent can be detected in vitro and with the selected detection method.

FIG. 2 C shows that an increase in the resveratrol concentration to total lipid/resveratrol 2.005/1.25 mol/mol considerably increases the fusion efficiency of the liposomes.

TABLE 1

Information about quantifies and volumes of components A, B and of the polyphenol C as well as of the solvents (MW = molecular weight; stock = parent solution).

| Component | MW [g/mol] | $C_{Stock}$ [mg/ml] | Solvent | Mol ratio [mol/mol] | m [µg] | V [µl] |
|---|---|---|---|---|---|---|
| DOPE (molecule of type B) | 744.03 | 1 | chloroform/EtOH | 1 | 515 | 515 |
| DOTAP (A) | 698.54 | 1 | chloroform/EtOH | 1 | 485 | 485 |
| BFL-DHPE[1] | 1067.23 | 1 | chloroform | 0.005 | 4 | 4 |
| Resveratrol (polyphenol C) | 228.24 | 1 | EtOH | a. 0 | 0 | 0 |
|  |  |  |  | b. 0.62 | 100 | 100 |
|  |  |  |  | c. 1.25 | 200 | 200 |
|  |  |  |  | d. 2.5 | 300 | 300 |

[1]not part of the morecule mixture, but only present for detecting fusion.

This results in four batches comprising a total lipid made of molecules of types A and B and BODIPY® FL-DHPE/resveratrol ratios of
 a) 2.005/0 mol/mol (control)
 b) 2.005/0.62 mol/mol
 c) 2.005/1.25 mol/mol and
 d) 2.005/2.5 mol/mol.

Starting at this concentration of resveratrol, the optimal range of a fusion exists under the analysis conditions in question, which is to say in vitro.

FIG. 2 D shows that unchanged cell morphology was observed, in addition to a high fusion rate, at double the resveratrol concentration and a total lipid/resveratrol ratio=2.005/2.5.

Concentrations that went beyond this were not analyzed, since the polyphenol C cannot be introduced into the liposomes with higher effectiveness at a molecular ratio greater than 1:1:5 mol/mol, and consequently no improved therapeutic effect over neutral vesicles can be detected.

Therefore, it goes without saying that:
1. resveratrol, or the polyphenol C, itself triggers the fusion in the liposome membrane; and
2. the phenol components present in the aqueous, liposomal phase are transferred into the cell, and in particular into the cell membrane, after the fusion process and can be used effectively there as a therapeutic agent for diseases based on oxidative stress, for example as a tumor-treating drug; and
3. considerably different concentrations of the polyphenol C are to be expected in vivo. Here, molecular ratios of A:B:C of $1(\pm 0.2):1(\pm 0.2):0.1\text{-}25$ mol/mol, or the above-mentioned intermediate values, should be selected and combined so as to achieve the optimal action result for the corresponding experiments.

These measures thus represent an effective mechanism for treating all oxidative disease processes in the cells.

2-112 Exemplary Embodiment

The remaining exemplary embodiments disclosed in this patent application for molecules of type A, molecules of type B and the polyphenol C, as described in claims 2 to 4, are combined and mixed with each other, wherein a total of 112 combinations are possible. The molar ratio and solvent correspond to those of Exemplary Embodiment 1. This results in molecule mixtures 2-112, which, as with Mixture 1 of Exemplary Embodiment 1, can be used as liposomes for use in tumor treatment or in other oxidative diseases.

Figure 3:
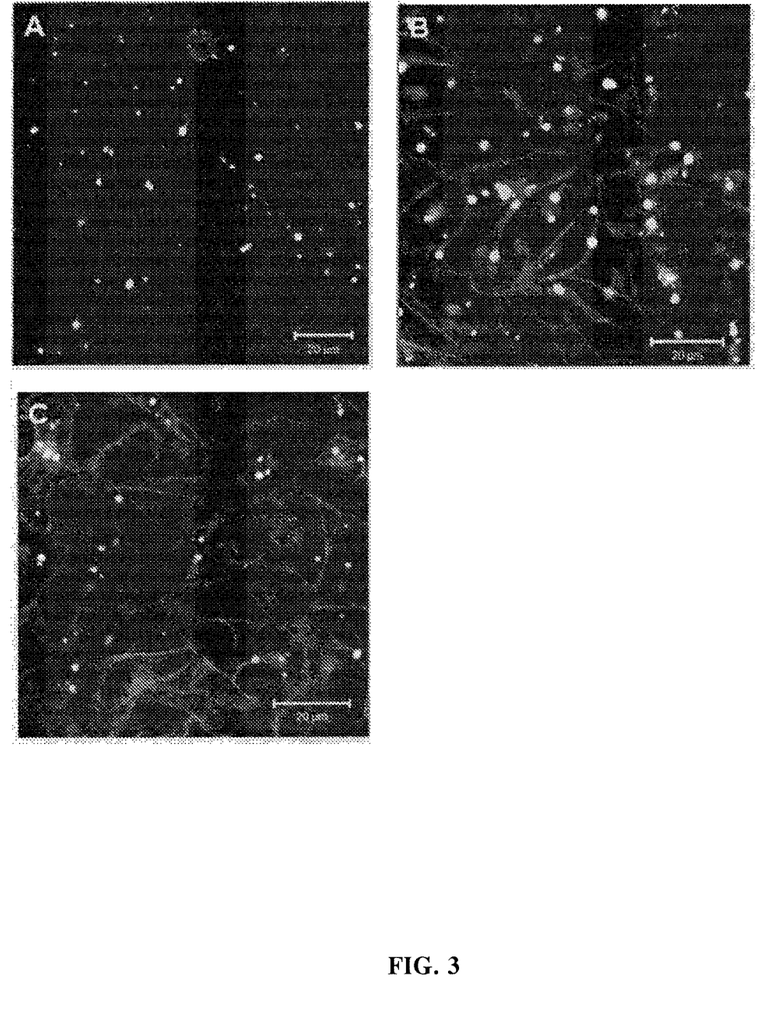

The following additional experiments are mentioned by way of example, and the results thereof are shown in FIG. 3:

The polyphenols listed in the patent application in addition to resveratrol, such as curcumin and 5-hydroxyflavone, were tested on CHO (Chinese hamster ovary) cells. The liposome preparation and the cell culture methods were not changed compared to the preceding experiments.

FIG. 3 A shows that the positively charged liposomes without polyphenol (DOPE/DOTAP/BODIPY FL-DHPE 1/1/0.005 mol/mol) also do not trigger any membrane fusion with CHO (Chinese hamster ovary) cells. The following molecule mixture was used for this purpose: DOTAP:DOPE:BODIPY FL-DHPE of 1:1:0.005 mol/mol. BODIPY FL-DHPE is not part of the molecule mixture, but only present for detecting the fusion.

FIG. 3 B shows that an increase in the polyphenol concentration, which here is curcumin, to total lipid/curcumin=2.005/1.25 mol/mol increases the fusion efficiency of the liposomes with the plasma membrane of the CHO cells just as considerably as resveratrol. The following molecule mixture was used for this purpose: DOTAP:DOPE:BODIPY-FL-DHPE:curcumin of 1:1:0.005:1.5 mol/mol. BODIPY FL-DHPE is not part of the molecule mixture, but only present for detecting the fusion.

FIG. 3 C shows that the fusion rate after use of 5-hydroxyflavone-containing liposomes (total lipid/5-hydroxyflavone=2.005/1.25 mol/mol) on CHO (Chinese hamster ovary) cells is just as high as with the preceding polyphenols. The following molecule mixture was used for this purpose: DOTAP:DOPE:BODIPY FL-DHPE:5-hydroxyflavone of 1:1:0.005:1.5 mol/mol. BODIPY FL-DHPE is not part of the molecule mixture, but is present only for detecting the fusion.

Another object of the invention is further achieved by molecule mixtures and methods for the production thereof, in which the molecules of types A and B and the polyphenol C are present in, or adjusted to, a molecular ratio of $1(\pm 0.2):1(\pm 0.2):0.5\text{-}2.5$ mol/mol, in particular at a molecular ratio of A:B:C of $1(\pm 0.2):1(\pm 0.2):0.62\text{-}2.5$ mol/mol, and in particular at a molecular ratio of A:B:C of $1(\pm 0.2):1(\pm 0.2):1.25\text{-}2.5$ mol/mol.

It is also conceivable to administer all the described exemplary embodiments also in powdered tablet form, if the transfer into the aqueous liposomal phase is dispensed with.

The invention claimed is:

1. A liposome for delivery of an antioxidant to a cell comprising a molecule mixture comprising (A) a first amphipathic molecule, which has an overall positive charge in the hydrophilic region, (B) a second amphipathic molecule, which is neutral in the hydrophilic region, and (C) a polyphenol selected from resveratrol, curcumin, hydroxyflavone, genistein, or a mixture thereof,
   wherein the molecules (A), (B) and (C) are present at a molecular ratio (A):(B):(C) of $1(\pm 0.2):1(\pm 0.2):1.25\text{-}2.50$ mol/mol, the liposome having a membrane and a portion interior to the membrane, and wherein a majority portion of the polyphenol (C) is within the membrane and a smaller portion than the majority portion is within the liposome interior portion.

2. The liposome according to claim 1, wherein the first amphipathic molecule (A) is selected from 1,2-dioleoyl-3-trimethylammonium propane (DOTAP), N-(2,3-dioleyloxypropyl)-N,N,N-trimethylammonium chloride (DOTMA), dimethyl dioctadecyl ammonium bromide (DDAB), (1-[2-(oleoyloxy)ethyl]-2-oleyl-3-(2-hydroxyethyl)imidazolinium chloride (DOTIM), or a mixture thereof.

3. The liposome according to claim 1, wherein the second amphipathic molecule (B) is selected from 1,2-dioleoyl-sn-glycero-3-phosphoethanolamine, 1,2-dipalmitoyl-sn-glycero-3-phosphoethanolamine, 1,2-dimiristoyl-sn-glycero-3-phosphoethanolamine, 1,2-dielaidoyl-sn-glycero-3-phosphoethanolamine, 1,2-diphytanol-sn-glycero-3-phosphoethanolamine, 1,2-dilinoleoyl-sn-glycero-3-phosphoethanolamine, 1,2-dioleoyl-sn-glycero-3-phosphatidylcholine, or a mixture thereof.

4. The liposome according to claim 1, wherein the mixture is present as a liposome in an aqueous environment.

5. A method for producing a liposome for delivery of an antioxidant to a cell, the liposome comprising a molecule mixture comprising (A) a first amphipathic molecule, which has an overall positive charge in the hydrophilic region, (B) a second amphipathic molecule, which is neutral in the hydrophilic region, and (C) a polyphenol selected from resveratrol, curcumin, hydroxyflavone, genistein, or a mixture thereof,
   wherein the molecules (A), (B) and (C) are present at a molecular ratio (A):(B):(C) of $1(\pm 0.2):1(\pm 0.2):1.25\text{-}2.50$ mol/mol, the liposome having a membrane and a portion interior to the membrane, and wherein a majority portion of the polyphenol (C) is within the membrane and a smaller portion than the majority portion is within the liposome interior portion,
   the method comprising the following steps:
   a.) dissolving the first and second amphipathic molecules (A) and (B) in an organic solvent to form a first mixture;
   b.) dissolving and mixing the polyphenol (C) separately from the first and second amphipathic molecules (A) and (B) in another organic solvent; to form a second mixture separate from the first mixture;
   c.) after steps a) and b), mixing the first mixture comprising the first and second amphipathic molecules (A) and (B) and the second mixture comprising the polyphenol (C) with each other and homogenizing them to form a third mixture, wherein in step c) the molecular ratio (A):(B):(C) is of 1(±0.2):1(±0.2):1.25.-2.50 mol/mol;
d.) removing said organic solvent and said another organic solvent from the third mixture; and
e.) re-suspending the third mixture in a water-based buffer, whereby the liposome is produced.

6. The method according to claim 5, wherein methanol or ethanol is the solvent for the polyphenol (C) and chloroform, ethanol, methanol or a mixture thereof is the solvent for the first and second amphipathic molecules (A) and (B).

7. The method according to claim 5, further comprising before the step (e) the step of transferring the molecule mixture to the water-based buffer.

8. A drug comprising the liposome according to claim 1.

9. A composition for delivery of therapeutic agents comprising a liposome in an aqueous medium that includes a buffer, the liposome comprising a molecule mixture comprising (A) a first amphipathic molecule, which has an overall positive charge in the hydrophilic region, (B) a second amphipathic molecule, which is neutral in the hydrophilic region, and (C) a polyphenol selected from resveratrol, curcumin, hydroxyflavone, genistein, or a mixture thereof,
wherein the molecules (A), (B) and (C) are present at a molecular ratio (A):(B):(C) of 1(±0.2):1.25.-2.50 mol/mol, wherein the liposome comprises a membrane and a portion interior to the membrane, the membrane containing a majority portion of (C) the polyphenol and the interior portion containing a smaller portion of the polyphenol.

10. The method of claim 5, wherein the organic solvent into which the first and second amphipathic molecules are dissolved in step a) has a different composition as said another organic solvent into which the polyphenol is dissolved in step b).

11. The liposome of claim 1, wherein the polyphenol is resveratrol.

12. The liposome of claim 1, wherein the polyphenol is curcumin.

13. The liposome of claim 1, wherein the polyphenol is 5-hydroxyflavone.

14. The method of claim 5, wherein the polyphenol is resveratrol and wherein said dissolving and mixing the polyphenol (C) is dissolving and mixing the resveratrol separately from the first and second amphipathic molecules (A) and (B) in another organic solvent; to form a second mixture separate from the first mixture.

15. The method of claim 5, wherein the polyphenol is curcumin and wherein said dissolving and mixing the polyphenol (C) is dissolving and mixing the curcumin separately from the first and second amphipathic molecules (A) and (B) in another organic solvent; to form a second mixture separate from the first mixture.

16. The method of claim 5, wherein the polyphenol is 5-hydroxyflavone and wherein said dissolving and mixing the polyphenol (C) is dissolving and mixing the 5-hydroxyflavone separately from the first and second amphipathic molecules (A) and (B) in another organic solvent; to form a second mixture separate from the first mixture.

\* \* \* \* \*

UNITED STATES PATENT AND TRADEMARK OFFICE
CERTIFICATE OF CORRECTION

PATENT NO. : 9,610,254 B2  Page 1 of 1
APPLICATION NO. : 14/241155
DATED : April 4, 2017
INVENTOR(S) : Agnes Csiszar et al.

It is certified that error appears in the above-identified patent and that said Letters Patent is hereby corrected as shown below:

On the Title Page

After item (65) before item (51), insert item (30), as follows:
--(30) Foreign Application Priority Data
Oct. 6, 2011 (DE) 10 2011 114 951.5.--

Signed and Sealed this
Thirtieth Day of May, 2017

Michelle K. Lee
*Director of the United States Patent and Trademark Office*